(12) United States Patent
Fuller

(10) Patent No.: US 11,771,583 B1
(45) Date of Patent: Oct. 3, 2023

(54) ARM-CASTING STAND

(71) Applicant: Kevin Fuller, Conyers, GA (US)

(72) Inventor: Kevin Fuller, Conyers, GA (US)

(*) Notice: Subject to any disclaimer, the term of this patent is extended or adjusted under 35 U.S.C. 154(b) by 581 days.

(21) Appl. No.: 17/027,808

(22) Filed: Sep. 22, 2020

(51) Int. Cl.
*A61G 13/12* (2006.01)
*A61F 5/37* (2006.01)
*A61F 5/01* (2006.01)

(52) U.S. Cl.
CPC .......... *A61F 5/3761* (2013.01); *A61F 5/0118* (2013.01); *A61G 13/124* (2013.01); *A61G 13/1235* (2013.01)

(58) Field of Classification Search
CPC .......................... A61G 13/1235; A61G 13/124
USPC ............ 248/118, 118.1, 118.3, 118.5; 5/623; 128/878, 879, 881
See application file for complete search history.

(56) References Cited

U.S. PATENT DOCUMENTS

| | | |
|---|---|---|
| 1,891,755 A | 12/1932 | Davis |
| 3,020,909 A | 2/1962 | Stevens |
| 4,941,463 A | 7/1990 | Dergenroeder |
| 5,169,103 A * | 12/1992 | Jimenez ................. A45D 29/18 132/73 |
| 5,242,140 A | 9/1993 | Ritland |
| 5,518,213 A | 5/1996 | Hairston |
| 6,070,838 A * | 6/2000 | Luginsland ........ A47B 21/0371 248/118.5 |
| 6,347,771 B1 * | 2/2002 | Lauzon ............. A47B 21/0371 248/118 |
| D518,894 S | 4/2006 | Kim |
| 8,043,241 B2 * | 10/2011 | Goumas ................. A61F 5/3738 128/892 |
| 2009/0000625 A1 * | 1/2009 | Alfery ................... A61F 5/3761 128/878 |
| 2014/0059772 A1 * | 3/2014 | Crisco .................... A61G 5/125 5/623 |
| 2018/0055708 A1 * | 3/2018 | Hatch .................. A61G 13/124 |
| 2021/0386577 A1 * | 12/2021 | Bleau .................... A61F 5/3753 |

FOREIGN PATENT DOCUMENTS

CA 2325749 5/2002

* cited by examiner

*Primary Examiner* — Alfred J Wujciak
(74) *Attorney, Agent, or Firm* — Kyle A. Fletcher, Esq.

(57) ABSTRACT

The arm-casting stand may comprise a base, an elbow cushion, a horizontal armature, an arm support, and a vertical armature. The arm-casting stand may be adapted to support and position an arm of a patient while a medical procedure is performed. The arm-casting stand may eliminate the need for a staff member to manually support the arm and may enhance the comfort of the patient. The base may be placed upon a work surface adjacent to the patient. The elbow cushion may be adapted for resting a portion of the arm upon. The elbow cushion may be held at a specific position relative to the base by the horizontal armature. The arm support may be adapted for elevating a portion of the arm. The arm support may be held at a specific position relative to the base by the vertical armature.

18 Claims, 4 Drawing Sheets

ARM-CASTING STAND

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical accessories, more specifically, an arm-casting stand.

SUMMARY OF INVENTION

The arm-casting stand may comprise a base, an elbow cushion, a horizontal armature, an arm support, and a vertical armature. The arm-casting stand may be adapted to support and position an arm of a patient while a medical procedure is performed. The arm-casting stand may eliminate the need for a staff member to manually support the arm and may enhance the comfort of the patient. The base may be placed upon a work surface adjacent to the patient. The elbow cushion may be adapted for resting a portion of the arm upon. The elbow cushion may be held at a specific position relative to the base by the horizontal armature. The arm support may be adapted for elevating a portion of the arm. The arm support may be held at a specific position relative to the base by the vertical armature.

An object of the invention is to support and position an arm of a patient during a medical procedure.

Another object of the invention is to provide an elbow cushion to support an elbow.

A further object of the invention is to provide an arm support to support and constrain an arm.

Yet another object of the invention is to provide a horizontal armature and a vertical armature to allow repositioning of the elbow cushion and the arm support, respectively.

These together with additional objects, features and advantages of the arm-casting stand will be readily apparent to those of ordinary skill in the art upon reading the following detailed description of the presently preferred, but nonetheless illustrative, embodiments when taken in conjunction with the accompanying drawings.

In this respect, before explaining the current embodiments of the arm-casting stand in detail, it is to be understood that the arm-casting stand is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the arm-casting stand.

It is therefore important that the claims be regarded as including such equivalent construction insofar as they do not depart from the spirit and scope of the arm-casting stand. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

Figure 1:
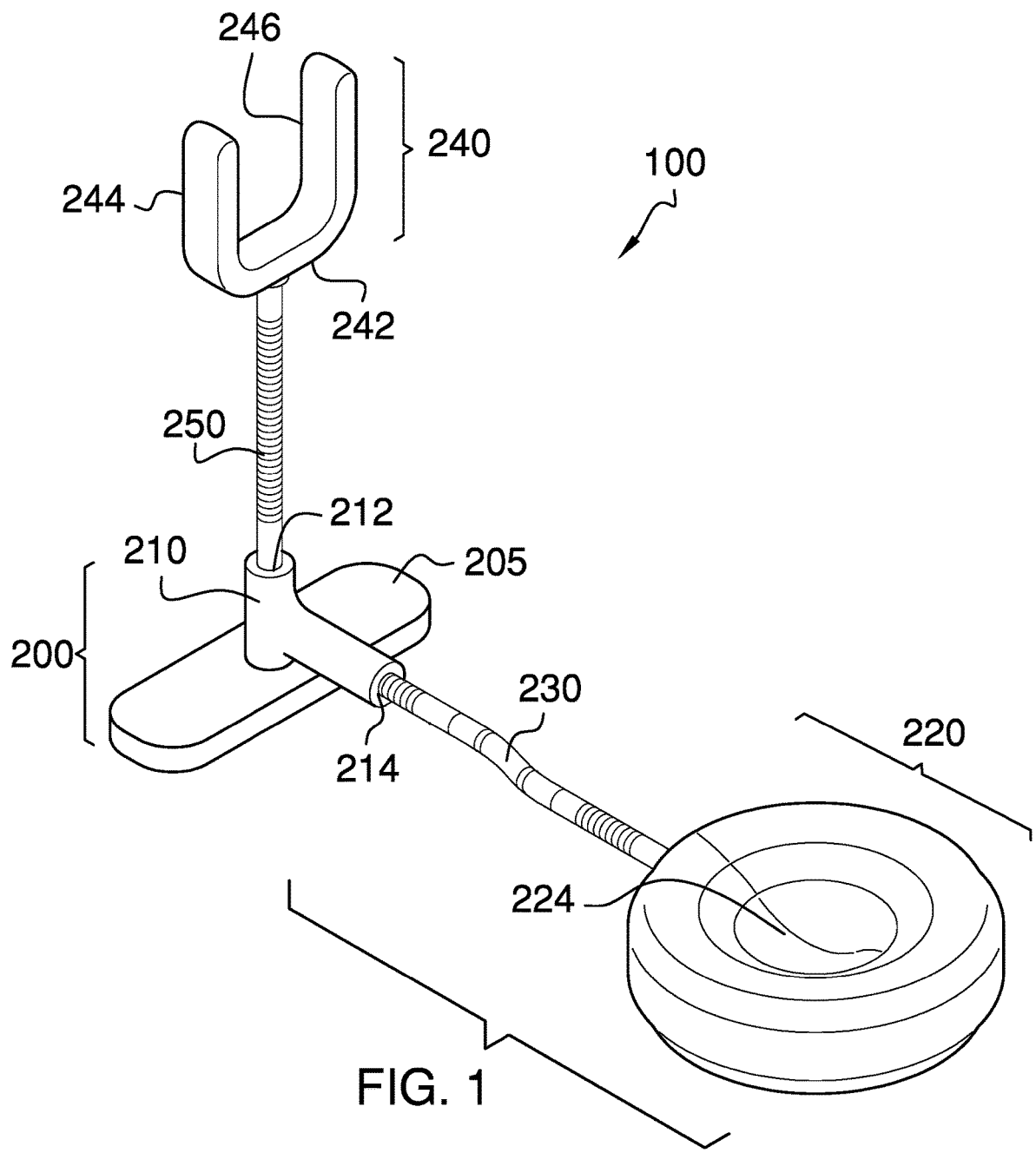
FIG. 1 is an isometric view of an embodiment of the disclosure.
Figure 2:
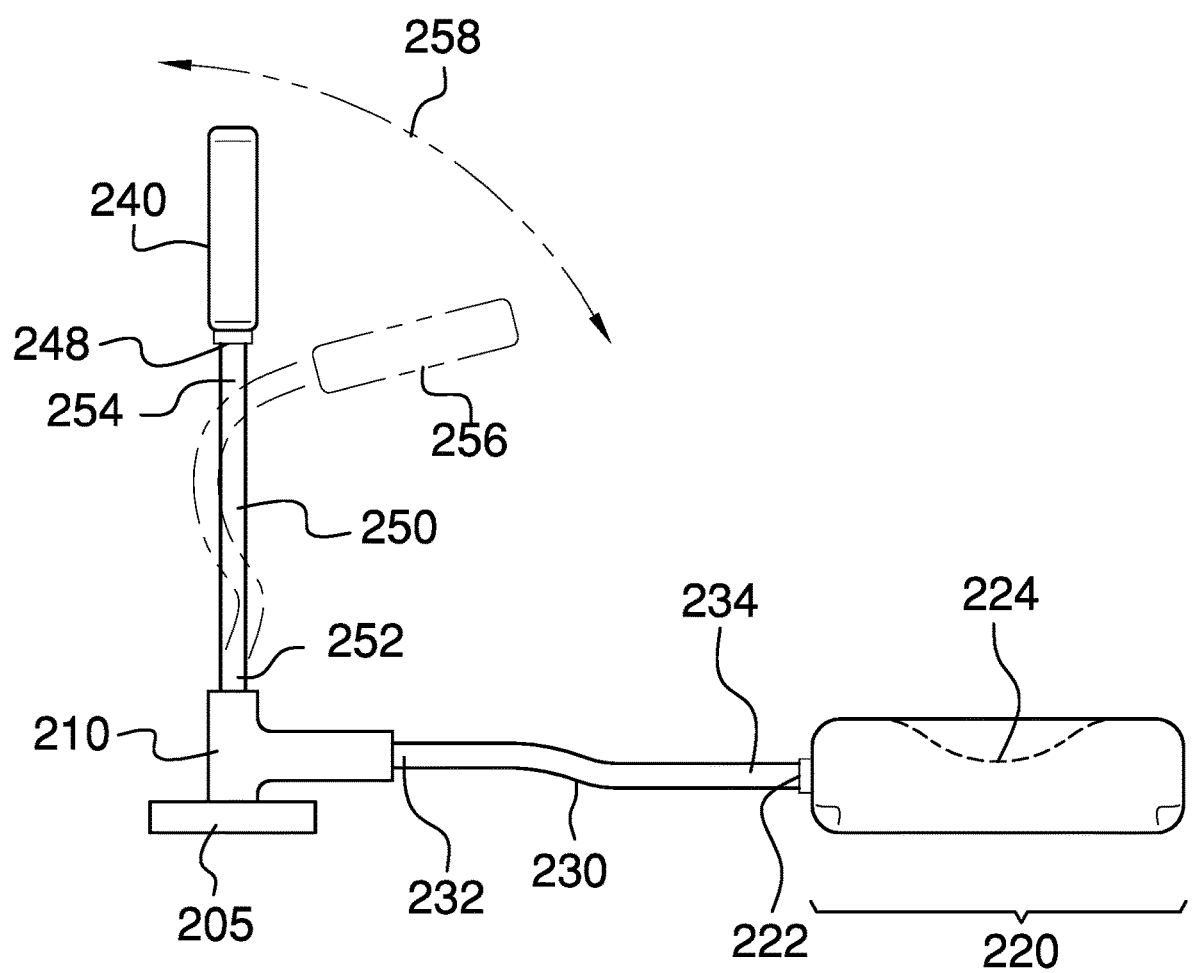
FIG. 2 is a side view of an embodiment of the disclosure.
Figure 3:
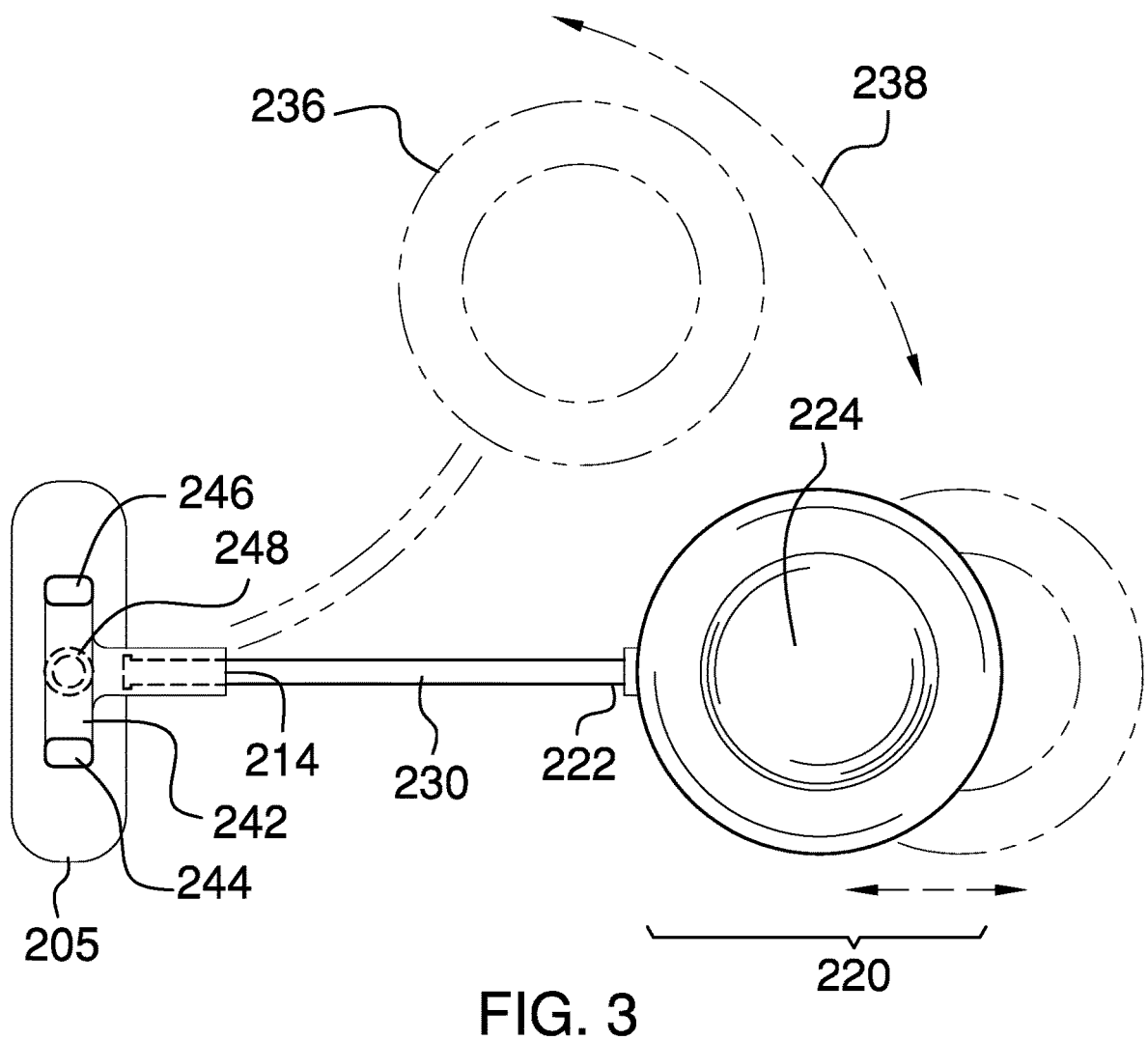
FIG. 3 is a top view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. As used herein, the word "or" is intended to be inclusive.

Detailed reference will now be made to a first potential embodiment of the disclosure, which is illustrated in FIGS. 1 through 4.

The arm-casting stand 100 (hereinafter invention) comprises a base 200, an elbow cushion 220, a horizontal armature 230, an arm support 240, and a vertical armature 250. The invention 100 may be adapted to support and position an arm 910 of a patient 900 while a medical procedure is performed. As non-limiting examples, the medical procedure may be the application or removal of a cast or splint. The invention 100 may eliminate the need for a staff member to manually support the arm 910 and may enhance the comfort of the patient 900. The base 200 may be placed upon a work surface 930. The patient 900 may be seated adjacent to the work surface 930. The elbow cushion 220 may be adapted for resting a portion of the arm 910 upon. As a non-limiting example, the patient 900 may rest an elbow 912 on the elbow cushion 220. The elbow cushion 220 may be held at a specific position relative to the base 200 by the horizontal armature 230. The arm support 240 may be adapted for elevating a portion of the arm 910. As a non-limiting example, the arm support 240 may support a forearm 914 of the patient 900. The arm support 240 may be held at a specific position relative to the base 200 by the vertical armature 250.

The base 200 may support the vertical armature 250 and may serve as a positional reference point for the elbow cushion 220 and the arm support 240. The base 200 may comprise a foot 205 and a coupler 210. The foot 205 may rest upon the work surface 930. The bottom of the coupler 210 may couple to the top of the foot 205. The coupler 210 may comprise a vertical interface 212 and a horizontal interface 214. The vertical interface 212 may be located on the top of the coupler 210. The horizontal interface 214 may be located on the side of the coupler 210. The coupler 210 may comprise the vertical interface 212 and the horizontal interface 214.

The elbow cushion 220 may rest upon the work surface 930. The elbow cushion 220 may be adapted to support the elbow 912 when the elbow 912 is rested on top of the elbow cushion 220. The top of the elbow cushion 220 may be padded for comfort. In a preferred embodiment, the elbow cushion 220 may be a disk-shape element having a circular footprint. The elbow cushion 220 may comprise an elbow interface 222. The elbow interface 222 may be located on the side of the elbow cushion 220.

In some embodiments, the elbow cushion 220 may comprise a divot 224. The divot 224 may be a depression in the top surface of the elbow cushion 220. The divot 224 may be adapted to center the elbow 912 on the elbow cushion 220. The padding on the top of the elbow cushion 220 may cover the divot 224.

The horizontal armature 230 may be a pliable armature that couples the coupler 210 to the elbow cushion 220. Specifically, a first end of the horizontal armature 232 may couple to the horizontal interface 214 on the coupler 210 and a second end of the horizontal armature 234 may couple to the elbow interface 222 on the elbow cushion 220. The horizontal armature 230 may bend when an external horizontal armature bending force 238 is applied to the horizontal armature 230 or to the elbow cushion 220 such that the elbow cushion 220 may move to a new elbow cushion position 236. The elbow cushion 220 may maintain the new elbow cushion position 236 when the external horizontal armature bending force 238 is removed. Movement of the elbow cushion 220 to the new elbow cushion position 236 may change the distance between the elbow cushion 220 and the arm support 240, the distance between the coupler 210 and the elbow cushion 220, or both.

The arm support 240 may be adapted to support and/or constrain the arm 910. As a non-limiting example, the arm support 240 may be a U-shaped armature comprising a crossbar 242, a first upright 244, and a second upright 246. The crossbar 242 may be adapted to provide vertical support for the arm 910 while the first upright 244 and the second upright 246 provide constrain of horizontal motion.

Figure 4:
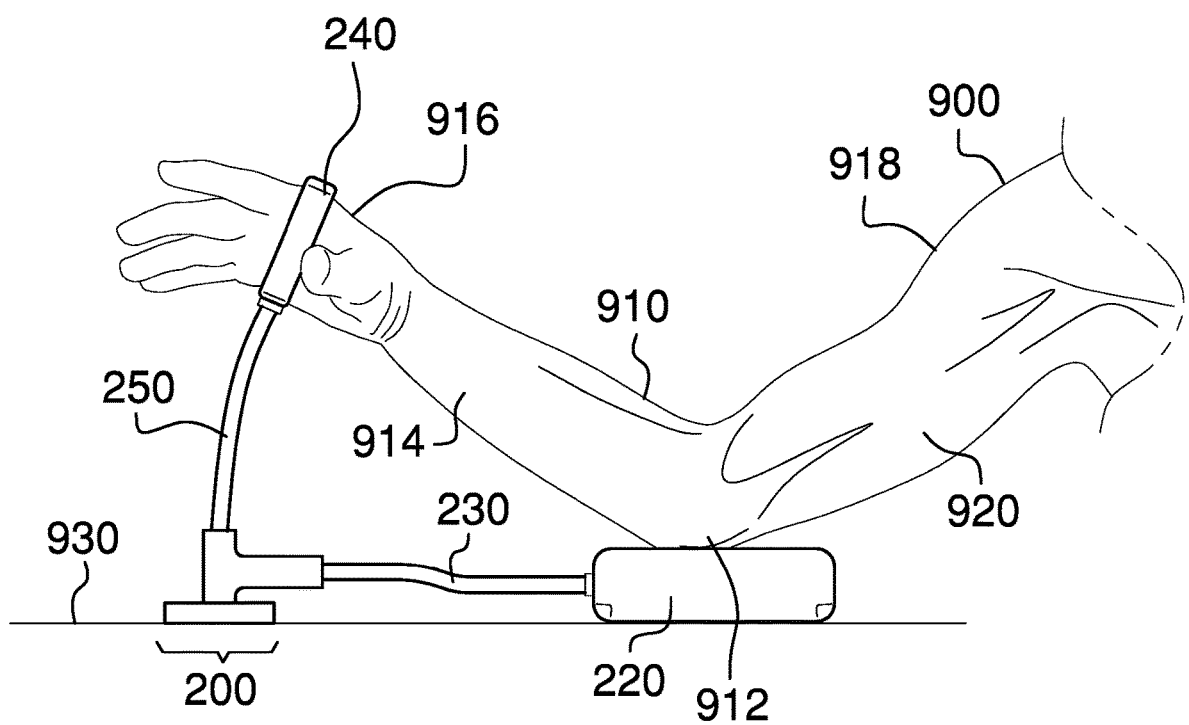
FIG. 4 is an in-use view of an embodiment of the disclosure illustrating an elbow resting on the elbow cushion and a forearm resting on the arm support.

As a non-limiting example, the arm support 240 may be adapted to support and constrain motion of the forearm 914. FIG. 4 illustrates a hand 916 supported and constrained by the arm support 240 while the elbow 912 is supported by the elbow cushion 220.

As a non-limiting example, the arm support 240 may be adapted to support and constrain motion of an upper arm 920 between a shoulder 918 and the elbow 912.

The bottom of the arm support 240 may comprise an arm interface 248. The vertical armature 250 may couple to the arm interface 248.

In some embodiments, the arm support 240 may be padded for comfort.

The vertical armature 250 may be a pliable armature that couples the coupler 210 to the arm support 240. Specifically, a first end of the vertical armature 252 may couple to the vertical interface 212 on the coupler 210 and a second end of the vertical armature 254 may couple to the arm interface 248 on the arm support 240. The vertical armature 250 may bend when an external vertical armature bending force 258 is applied to the vertical armature 250 or to the arm support 240 such that the arm support 240 may move to a new arm support position 256. The arm support 240 may maintain the new arm support position 256 when the external vertical armature bending force 258 is removed. Movement of the arm support 240 to the new arm support position 256 may change the distance between the elbow cushion 220 and the arm support 240, the distance between the coupler 210 and the arm support 240, or both.

In some embodiment, the coupling between the horizontal interface 214 and the first end of the horizontal armature 232, the vertical interface 212 and the first end of the vertical armature 252, the elbow interface 222 and the second end of the horizontal armature 234, the arm interface 248 and the second end of the vertical armature 254, or combinations thereof may be detachable couplings. As non-limiting examples, the detachable couplings may be threaded couplings, press fit couplings, magnetic couplings, twist lock couplings, quick release couplings, or combinations thereof.

In use, the invention 100 may be placed on the work surface 930 and the patient 900 may be seated next to the work surface 930. The elbow cushion 220 and the arm support 240 may be repositioned in consideration of the type of procedure to be performed and in consideration of the size of the patient 900 The elbow cushion 220 may be repositioned by applying the external horizontal armature bending force 238 to the elbow cushion 220 or to the horizontal armature 230. The arm support 240 may be repositioned by applying the external vertical armature bending force 258 to the arm support 240 or to the vertical armature 250. For some procedures, the patient 900 may place the elbow 912 on the elbow cushion 220 and the hand 916 in the arm support 240.

Definitions

Unless otherwise stated, the words "up", "down", "top", "bottom", "upper", and "lower" should be interpreted within a gravitational framework. "Down" is the direction that gravity would pull an object. "Up" is the opposite of "down". "Bottom" is the part of an object that is down farther than any other part of the object. "Top" is the part of an object that is up farther than any other part of the object. "Upper" may refer to top and "lower" may refer to the bottom. As a non-limiting example, the upper end of a vertical shaft is the top end of the vertical shaft.

As used herein, the words "couple", "couples", "coupled" or "coupling", may refer to connecting, either directly or indirectly, and does not necessarily imply a mechanical connection.

As used here, "footprint" may refer to a vertical, downward projection of an object onto the surface that supports the object. The portion of the supporting surface that is within the footprint is, by definition, underneath the object.

As used herein, the term "friction fit" may refer to a type of mechanical coupling where a first component presses into a second component and is held there only by the friction of the first component against the second component. A friction fit may also be known as an interference fit or a press fit.

As used in this disclosure, "horizontal" may be a directional term that refers to a direction that is perpendicular to the local force of gravity. Unless specifically noted in this disclosure, the horizontal direction is always perpendicular to the vertical direction.

As used in this disclosure, a "patient" may be a person who is designated to receive a medical treatment, therapy or service. The term patient may be extended to an animal when used within the context of the animal receiving veterinary treatment or services As used herein, "pliable" may refer to an object or material which will deform when a force is applied to it, which will not return to its original shape when the deforming force is removed, and which may retain the deformed shape caused by the deforming force.

As used in this disclosure, "vertical" may refer to a direction that is parallel to the local force of gravity. Unless specifically noted in this disclosure, the vertical direction is always perpendicular to horizontal.

With respect to the above description, it is to be realized that the optimum dimensional relationship for the various components of the invention described above and in FIGS. 1 through 4, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An arm-casting stand comprising:
a base, an elbow cushion, a horizontal armature, an arm support, and a vertical armature;
wherein the arm-casting stand is adapted to support and position an arm of a patient while a medical procedure is performed;
wherein the base is placed upon a work surface;
wherein the elbow cushion is adapted for resting a portion of the arm upon;
wherein the elbow cushion is held at a specific position relative to the base by the horizontal armature;
wherein the arm support is adapted for elevating a portion of the arm;
wherein the arm support is held at a specific position relative to the base by the vertical armature;
wherein the base supports the vertical armature and serves as a positional reference point for the elbow cushion and the arm support;
wherein the base comprises a foot and a coupler;
wherein the foot rests upon the work surface;
wherein the bottom of the coupler couples to the top of the foot;
wherein the coupler comprises a vertical interface and a horizontal interface;
wherein the vertical interface is located on the top of the coupler;
wherein the horizontal interface is located on the side of the coupler;
wherein the coupler comprises the vertical interface and the horizontal interface.

2. The arm-casting stand according to claim 1
wherein the elbow cushion rests upon the work surface;
wherein the elbow cushion is adapted to support an elbow when the elbow is rested on top of the elbow cushion;
wherein the top of the elbow cushion is padded for comfort.

3. The arm-casting stand according to claim 2
wherein the elbow cushion is a disk-shape element having a circular footprint.

4. The arm-casting stand according to claim 2
wherein the elbow cushion comprises an elbow interface;
wherein the elbow interface is located on the side of the elbow cushion.

5. The arm-casting stand according to claim 4
wherein the elbow cushion comprises a divot;
wherein the divot is a depression in the top surface of the elbow cushion;
wherein the divot is adapted to center the elbow on the elbow cushion;
wherein the padding on the top of the elbow cushion covers the divot.

6. The arm-casting stand according to claim 5
wherein the horizontal armature is a pliable armature that couples the coupler to the elbow cushion;
wherein a first end of the horizontal armature couples to the horizontal interface on the coupler and a second end of the horizontal armature couples to the elbow interface on the elbow cushion.

7. The arm-casting stand according to claim 6
wherein the horizontal armature bends when an external horizontal armature bending force is applied to the horizontal armature or to the elbow cushion such that the elbow cushion moves to a new elbow cushion position.

8. The arm-casting stand according to claim 7
wherein the elbow cushion maintains the new elbow cushion position when the external horizontal armature bending force is removed.

9. The arm-casting stand according to claim 8
wherein movement of the elbow cushion to the new elbow cushion position changes the distance between the elbow cushion and the arm support, the distance between the coupler and the elbow cushion, or both.

10. The arm-casting stand according to claim 8
wherein the arm support is adapted to support and/or constrain the arm.

11. The arm-casting stand according to claim 10
wherein the arm support is a U-shaped armature comprising a crossbar, a first upright, and a second upright;
wherein the crossbar is adapted to provide vertical support for the arm while the first upright and the second upright provide constrain of horizontal motion.

12. The arm-casting stand according to claim 11
wherein the bottom of the arm support comprises an arm interface;
wherein the vertical armature couples to the arm interface.

13. The arm-casting stand according to claim 12
wherein the arm support is padded for comfort.

14. The arm-casting stand according to claim 13
wherein the vertical armature is a pliable armature that couples the coupler to the arm support;
wherein a first end of the vertical armature couples to the vertical interface on the coupler and a second end of the vertical armature couples to the arm interface on the arm support.

15. The arm-casting stand according to claim 14
wherein the vertical armature bends when an external vertical armature bending force is applied to the vertical armature or to the arm support such that the arm support moves to a new arm support position.

16. The arm-casting stand according to claim 15 wherein the arm support maintains the new arm support position when the external vertical armature bending force is removed.

17. The arm-casting stand according to claim 16 wherein movement of the arm support to the new arm support position changes the distance between the elbow cushion and the arm support, the distance between the coupler and the arm support, or both.

18. The arm-casting stand according to claim 16 wherein the couplings between the horizontal interface and the first end of the horizontal armature, the coupling between the vertical interface and the first end of the vertical armature, the coupling between the elbow interface and the second end of the horizontal armature, the coupling between the arm interface and the second end of the vertical armature, or combinations thereof are detachable couplings.

* * * * *